(12) United States Patent
Flugelman et al.

(10) Patent No.: US 7,767,201 B2
(45) Date of Patent: Aug. 3, 2010

(54) VASCULAR CELLS GENETICALLY ALTERED TO OVER-EXPRESS ANGIOGENIC PROLIFERATION AND MATURATION FACTORS; TREATMENT OF ATHEROSCLEROSIS USING SAME

(75) Inventors: Moshe Y. Flugelman, Haifa (IL); Zoya Gluzman, Tal El (IL); Meir Preis, Haifa (IL); Belly Koren, Yokneam Ilit (IL); Tzafra Cohen, Haifa (IL); Adili Tsaba, Haifa (IL); Anat Weisz, Haifa (IL)

(73) Assignee: Multi-Gene Vascular Systems Ltd., Nazareth (IL)

( * ) Notice: Subject to any disclaimer, the term of this patent is extended or adjusted under 35 U.S.C. 154(b) by 579 days.

(21) Appl. No.: 10/429,093

(22) Filed: May 2, 2003

(65) Prior Publication Data

US 2004/0151707 A1    Aug. 5, 2004

Related U.S. Application Data

(63) Continuation-in-part of application No. 10/344,089, filed as application No. PCT/IL01/00733 on Aug. 8, 2001, now abandoned.

(60) Provisional application No. 60/223,727, filed on Aug. 8, 2000.

(51) Int. Cl.
*A61K 48/00* (2006.01)
*C12N 15/85* (2006.01)

(52) U.S. Cl. .................. 424/93.21; 435/455

(58) Field of Classification Search ............... 514/44; 424/93.2, 93.21; 435/455
See application file for complete search history.

(56) References Cited

U.S. PATENT DOCUMENTS

| | | | |
|---|---|---|---|
| 4,900,556 A | 2/1990 | Wheatley et al. | 424/450 |
| 4,950,483 A | 8/1990 | Ksander et al. | 424/422 |
| 5,219,739 A | 6/1993 | Tischer et al. | 435/69.4 |
| 5,618,544 A | 4/1997 | Brown | 424/401 |
| 5,665,567 A | 9/1997 | Eichner et al. | 435/69.4 |
| 5,674,722 A | 10/1997 | Mulligan et al. | 435/172.3 |
| 5,785,965 A * | 7/1998 | Pratt et al. | 424/93.21 |
| 5,941,868 A | 8/1999 | Kaplan et al. | 604/500 |
| 5,980,885 A | 11/1999 | Weiss et al. | 424/93.21 |
| 6,001,350 A | 12/1999 | Mulligan et al. | 424/93.21 |
| 6,007,987 A | 12/1999 | Cantor et al. | 435/6 |
| 6,099,832 A * | 8/2000 | Mickle et al. | 424/93.21 |
| 6,328,762 B1 * | 12/2001 | Anderson et al. | 623/1.41 |
| 6,554,857 B1 * | 4/2003 | Zilla et al. | 623/1.23 |
| 6,592,864 B1 * | 7/2003 | Stewart | 424/93.21 |
| 6,753,321 B2 | 6/2004 | Kovesdi | 514/44 |

FOREIGN PATENT DOCUMENTS

| | | |
|---|---|---|
| EP | 1 016 726 A1 | 7/2000 |
| WO | WO 93/23550 | 11/1993 |
| WO | WO 97/38729 | 10/1997 |
| WO | WO/98/15575 * | 4/1998 |
| WO | WO 00/12028 | 3/2000 |
| WO | WO 00/37642 | 6/2000 |
| WO | WO 02/083851 A2 | 10/2002 |

OTHER PUBLICATIONS

Suri et al., Cell, 1996, 87: 1171-1180.*
Parikh et al Adv Drug Deliv Rev. 2000; 42(1-2): 139-161.*
Srour et al., 1999 The Journal of hematotherapy 8:93-102.*
Fred G., Nature, 1998, 392: 18-24.*
Samstein et al. Journal of American Society of Nephrology, 2001, 12: 182-193.*
de Silva R, Lederman RJ. Cytotherapy. 2004; 6(6): 608-614; published as NIH public Access author manuscript , 2006, pp. 1-12.*
Jain RK, Munn LL. Nat Med. 2000; 6(2):131-132.*
Huang et al Biochem Biophys Res Commun. 1999; 264(1):133-8.*
Liddell et al Journal of Vascular and Interventional Radiology 16:991-998 , 2005.*
Fillinger et al J Surg Res. Feb. 1, 1997;67(2):169-78.*
Papapetropoulos et al J Biol Chem. Mar. 31, 2000;275(13):9102-5.*
Thurston et al Science, 1999, 286, 2511-2514.*
Chae et al Arterioscler Thromb Vasc Biol. 2000; 20(12):2573-8.*
Agha-Mohammadi et al. *J. Clin. Invest.*, 105(9):1177-1183 (2000).
Carmeliet et al. *Nature*, 383:73-75 (1996).
Cosset et al. *J. Virol.*, 69(12):7430-7436 (1995).
Dumont et al. *Genes Dev.*, 8(16):1897-1909 (1994).
Ferrara et al. *Nature*, 380:439-442 (1996).
Fong et al. *Nature*, 376:66-70 (1995).
Hanahan, D. *Science*, 277:48-50 (1997).
Jain et al. *Nat. Med.*, 6(2):131-132 (2000).
Leveen et al. *Genes Dev.*, 8(16):1875-1887 (1994).
Lindahl et al. *Science*, 277:242-245 (1997).
Maisonpierre et al. *Science*, 277:55-60 (1997).
Marandin et al. *Hum. Gene Ther.*, 9(10):1497-1511 (1998).
Markowitz et al. *Virology*, 167(2):400-406 (1988).
Miller et al. *Meth. Enzymol.*, 217(Part H):581-599 (1993).
Miller et al. *J. Virol.*, 70(8):5564-5571 (1996).
Naviaux et al. *J. Virol.*, 70(8):5701-5705 (1996).
Sato et al. *Nature*, 376:70-74 (1995).
Shalaby et al. *Nature*, 376:62-66 (1995).
Thurston et al. *Nat. Med.*, 6(4):460-463 (2000).

(Continued)

Primary Examiner—Deborah Crouch
Assistant Examiner—Anoop Singh
(74) Attorney, Agent, or Firm—Mintz, Levin, Cohn, Ferris, Glovsky and Popeo, P.C.; Ivor R. Elrifi; Matthew Pavao

(57) ABSTRACT

This invention relates to a method for producing angiogenesis in a tissue of a patient by administering vascular cells genetically altered to over-express an angiogenic proliferation factor and an angiogenic maturation factor to the affected tissue.

3 Claims, No Drawings

OTHER PUBLICATIONS

Asahara et al., "Tie2 Receptor Ligands, Angiopoietin-1 and Angiopoietin-2 Modulate VEGF-Induced Postnatal Neovascularization", *Circ. Res.*, 83(3):233-240 (1998).

Ellis et al., "Down-regulation of Vascular Endothelial Growth Factor in Human colon Carcinoma Cell Lines by Antisense Transfection Decreases Endothelial Cell Proliferation", *Surgery*, 120(5):871-878 (1996).

Folkman, J., "Therapeutic Angiogenesis in Ischemic Limbs", *Circulation*, 97:1108-1110 (1998).

Gale et al., "Growth factors acting via endothelial cell-specific receptor tyrosine kinases: VEGFs, Angiopoietins, and ephrins in vascular development", *Genes Dev.*, 13:1055-1066 (1999).

GenBank Accession No. AB021221.1, Jun. 1999, 3 pages.

GenBank Accession No. D14012.1, Feb. 2003, 3 pages.

GenBank Accession No. X54936.1, Nov. 1991, 3 pages.

GenBank Accession No. NM_005429.2, Mar. 2009, 6 pages.

GenBank Accession No. S67291.1, Mar. 2001, 3 pages.

GenBank Accession No. XM_045426.1, Oct. 2001, 2 pages.

He et al., "A simplified system for generating recombinant adenoviruses", *Proc., Natl. Acad. Sci. U.S.A.*, 95:2509-2514 (1998).

Kalka et al., "Vascular Endothelial Growth Factor165 Gene Transfer Augments Circulating Endothelial Progenitor Cells in Human Subjects", *Circ. Res.*, 86:1198-1201 (2000).

Leung et al., "Vascular endothelial growth factor is a secreted angiogenic mitogen", *Science*, 246:1306-1309 (1989).

Lewis et al., "Angiogenesis by gene therapy: a new horizon for myocardial revascularization?", *Cardiovasc. Res.*, 35(3):490-497 (1997).

Mulligan, R.C., "The Basic Science of Gene Therapy", *Science*, 260:926-932 (1993).

Namiki et al., "Hypoxia Induces Vascular Endothelial Growth Factor in Cultured Human Endothelial Cells", *J. Biol. Chem.*, 270(52):31189-31195 (1995).

Resnick et al., "Platelet-derived growth factor B chain promoter contains a cis-acting fluid shear-stress-responsive element", *Proc., Natl. Acad. Sci. U.S.A..*, 90:4591-4595 (1993).

Shyu et al., "Direct Intramuscular Injection of Plasmid DNA Encoding Angiopoietin-1 but not Angiopoietin-2 Augments Revascularization in the Rabbit Ischemic Hindlimb", *Circ.*, 98:2081-2087 (1998).

Zhang, Y., "Expression of Human Flt3 Ligand and Thrombopoietin Genes in a Bone Marrow Stromal Cell Line by Internal Ribosome Entry Site (IRES) Sequence", *Zhonghua Xue Ye Xue Za Zhi* (*Chinese Journal of Hematologu*), English Abstract, 20(12):624-625 (1999).

\* cited by examiner

```
                              SEQUENCE LISTING

<160> NUMBER OF SEQ ID NOS: 2

<210> SEQ ID NO 1
<211> LENGTH: 27
<212> TYPE: DNA
<213> ORGANISM: Artificial
<220> FEATURE:
<223> OTHER INFORMATION: Primer for PCR of Ang-1 cDNA

<400> SEQUENCE: 1
agatcttcaa aaatctaaag gtcgaat                                          27

<210> SEQ ID NO 2
<211> LENGTH: 27
<212> TYPE: DNA
<213> ORGANISM: Artificial
<220> FEATURE:
<223> OTHER INFORMATION: Primer for PCR of Ang-1 cDNA

<400> SEQUENCE: 2
agatctgctg gcagtacaat gacagtt                                          27
```

VASCULAR CELLS GENETICALLY ALTERED TO OVER-EXPRESS ANGIOGENIC PROLIFERATION AND MATURATION FACTORS; TREATMENT OF ATHEROSCLEROSIS USING SAME

RELATED APPLICATION

This application is a continuation-in-part of U.S. application Ser. No. 10/344,089, filed 7 Feb. 2003, now abandoned which, in turn, is related to PCT Application No. PCT/IL01/00733, entitled "Nucleic Acid Constructs, Vascular Cells Transformed Therewith, Pharmaceutical Compositions and Methods Utilizing Same for Inducing Angiogenesis," filed 8 Aug. 2001, and to corresponding U.S. Provisional Application 60/223,727, filed 8 Aug. 2000, each of which is incorporated by reference, including any drawings, as if fully set forth herein.

FIELD OF THE INVENTION

The present invention relates to the fields of chemistry, biochemistry, cellular biology, genetic engineering and medicine. In particular, it relates to vascular cells genetically altered with nucleic acid constructs that express pro-angiogenic factors and their uses.

BACKGROUND OF THE INVENTION

Atherosclerosis is a condition characterized by irregularly distributed lipid deposits in the intima of large and medium-sized arteries. The deposits provoke fibrosis and calcification. Disorders involving atherosclerosis, such as coronary artery, cerebrovascular and peripheral vascular disease are the most common cause of death in the Western hemisphere. The World Health Organization (WHO) suggests that atherosclerosis-related diseases will be the leading cause of mortality in the world by the year 2020.

Various procedures are routinely used to treat atherosclerosis-related disorders such as bypass surgery and angioplasty. Although these are generally effective, they are highly invasive and complex to perform. In addition, they often do not succeed when the diseased region includes ischemic tissue, such as in the case of the blockage of an arterial tree or of a bypass graft. In such cases, an alternative, often concurrent, treatment is to stimulate the generation of new blood vessels to replace those damaged by the disease. Two types of new blood vessel formation occur naturally in adult human beings, recapitulated arteriogenesis and angiogenesis.

Recapitulated arteriogenesis involves the transformation of pre-existing arterioles into small muscular arteries. Angiogenesis is the sprouting of new blood vessels from existing ones. Angiogenesis occurs both in healthy individuals and those suffering from pathological conditions. An example of the former is the female reproductive cycle where angiogenesis occurs during the rebuilding of the lining of the uterus. An example of the latter is cancer where new blood vessels are formed in and around a growing tumor.

The angiogenic process is regulated by biomechanical and biochemical stimuli and occurs in three major stages. In the first stage, termed initiation, the connection between endothelial cells (EC) and the surrounding tissue is severed. In the second stage EC proliferate and invade the ischemic tissue, which results in formation of EC sprouts. In the third stage, the newly formed EC sprouts mature into functional blood vessels. Maturation of the blood vessels involves recruitment of cells that surround the endothelial cells such as pericytes in the capillaries, smooth muscle cells in larger vessels and cardiac myocytes in the heart. These cells provide structural support to the forming vessels and modulate their function.

The establishment and remodeling of blood vessels is controlled by paracrine signals, many of which are mediated by protein ligands that modulate the activity of transmembrane tyrosine kinase receptors. Among these ligands and receptors are vascular endothelial growth factor (VEGF) and its receptor families (VEGFR1 and VEGFR2), Angiopoietin 1 and 2 (Ang-1 and Ang-2) and their receptor (Tie 2), acidic and basic fibroblast growth factor (aFGF, bFGF), platelet derived growth factor (PDGF), transforming growth factors α and β (TGF-α, TGF-β) and tumor necrosis factor α (TNF-α).

The role of VEGF and its receptors in preliminary stages of angiogenesis has been clearly demonstrated using VEGF receptor null heterozygous animals (Hanahan, D., *Science*, 1997, 277:48-50; Ferrara, N., Carver-Moore, K., Chen, H., et al., *Nature*, 1996, 380:439-42; Shalaby, F., Rossant, J., Yamaguchi, T. P., et al., *Nature*, 1995, 376:62-66). These animals, which do not survive the early stages of embryogenesis, either do not produce EC when heterozygous for the VEGFR1 receptor, or fail to form vessels when heterozygous for the VEGFR2 receptor. Studies in which the Tie2 receptor or its ligands Ang-1 and Ang-2 were disrupted demonstrated that although EC formed a tube, periendothelial cells were not recruited (Fong, G. H., Rossant, J., Gertenstein, M., et al., *Nature*, 376:66-70; Dumont, D. J., Gradwhol, G., Fong, G-H., et al., *Genes Dev.*, 1994, 8:1897-1903; Sato, T. N., Tzoawa, Y., Deutsch, U., et al., *Nature*, 1995, 376:70-74; Suri, C., Jones, P. F., Patan, S., et al., *Cell*, 1996, 87:1171-80; Maisonpierre, P. C., Suri, C., Jones, P. F., et al., *Science*, 1997, 277:55-60). A similar phenotype was observed in animals lacking PDGF-B, TGF-β and tissue factor (Leveen, P., Pekny, M., Gebre-Medhin, S., et al., *Genes Dev.*, 1994, 8:1875-87; Carmeliet, P., Mackman, N., Moons, L., et al., *Nature*, 1996, 383:73-75; Lindhal, P., Johansson, B. R., Leveen, P., Hbetsholtz, C., *Science*, 1997, 277:242-245) suggesting that the binding of angiopoietin to its receptor may lead to the secretion of these factors from the endothelium. Other studies have suggested that VEGF is responsible for the early stage of angiogenesis, which is characterized by disintegration of EC and leakage of plasma components (*Nat. Med.*, 2000, 6:131-2, 6:460-3). There are studies that suggest that Ang-1 regulates the maturation of newly formed blood vessels, while other studies suggest that the binding of Ang-2 to Tie2 plays a role in the regression of existing vessels (Suri, C., Jones, P. F., Patan, S, et al., *Cell*, 1996,87:1171-80).

Whether or not angiogenesis occurs in a particular situation is determined by changes in the local equilibrium among angiogenic modulators, i.e., stimulatory and inhibitory factors. In this regard, gene therapy, the insertion into cells of genes that express the modulators has received a great deal of attention. For example, gene therapy has been examined both in vitro and in vivo as a means for inhibiting smooth muscle cell proliferation following angioplasty or bypass surgery and for inducing angiogenesis by enhancement of EC cell proliferation. Naked-DNA and recombinant adenoviral vectors encoding $VEGF_{165}$ and $VEGF_{121}$ have been used to transfer genes in vivo to human patients suffering from ischemic and peripheral vascular disease to genetically modify endogenous vascular cells to express angiogenic factors.

Co-administration of VEGF and Ang-1 encoding vectors in an animal model has been shown to enhance the development of collateral vessels. However, as with the above methods, this approach would be expected to be of limited therapeutic utility in patient's with ischemic tissues and damaged organs because of a shortage of healthy cells to infect.

What is needed is a safe, effective method for inducing angiogenesis in tissue, in particular ischemic tissue. The present invention provides such a method using vascular cells genetically altered to over-express angiogenic and vascular maturation factors.

SUMMARY OF THE INVENTION

Thus, in one aspect, the present invention relates to a method for producing angiogenesis in a tissue of a patient in need thereof, comprising administering to the tissue a plurality of a first cell type that has been genetically altered with a first nucleic acid construct comprising a first polynucleotide sequence that expresses or over-expresses an angiogenic proliferating factor; and, administering to the tissue a plurality of a second cell type, which may be the same or different from the first cell type, that has been genetically altered with a second nucleic acid construct comprising a second polynucleotide sequence that expresses or over-expresses an angiogenic maturation factor.

In an aspect of this invention, the tissue is selected from the group consisting of an ischemic tissue, a narrowed or occluded vascular conduit and an injured vascular tissue.

In an aspect of this invention, the narrowed or occluded vascular conduit or tissue is a narrowed or occluded artery, narrowed or occluded vein or a narrowed or occluded synthetic graft.

In an aspect of this invention the first and second cell types are independently selected from the group consisting of endothelial cells, smooth muscle cells, pericytes, myocytes, monocytes, bone marrow stem cells, peripheal blood progenitors, fibroblasts, and embryonic stem cells.

In an aspect of this invention, the first cell type comprises endothelial cells and the second cell type comprises smooth muscle cells.

In an aspect of this invention, the cells are obtained from, or derived from cells of, the patient being treated.

In an aspect of this invention, the angiogenic proliferation factor is selected from the group consisting of VEGF, aFGF, bFGF, PlGF, leptin, HGF, VEGFR-1 and VEGFR-2.

In an aspect of this invention, the angiogenic maturation factor is selected from the group consisting of Ang-1, TGF-$\beta$1, TFG-$\beta$2, endoglin, Smad5, VE-cadherin, ephrinB2, PDGF, Bmx tyrosine kinase and MCP-1.

In an aspect of this invention, the angiogenic proliferation factor is VEGF and the angiogenic maturation factor is Ang-1.

In an aspect of this invention, the plurality of a first cell type comprises endothelial cells and the plurality of a second cell type comprises smooth muscle cells, wherein the plurality of endothelial cells express or over-express the Ang-1 and the plurality of smooth muscle cells express or over-express the VEGF.

In an aspect of this invention, the endothelial cells and the smooth muscle cells are administered in a 1:1 ratio.

In an aspect of this invention, plurality of the first cell type and the plurality of the second cell type are administered simultaneously.

In an aspect of this invention, the plurality of the first cell type is administered at least 12 hours before the plurality of the second cell type is administered.

In an aspect of this invention, the first nucleic acid construct further comprises a first promoter sequence that directs the expression of the angiogenic proliferation factor and the second nucleic acid construct further comprises a second promoter sequence that directs the expression of the angiogenic maturation factor.

In an aspect of this invention, the first and second promoters sequences are independently selected from the group consisting of a constitutive promoter sequence, an inducible promoter sequence and a tissue specific promoter sequence.

In an aspect of this invention, the first and second promoter sequences are the same.

In an aspect of this invention, the promoter sequence up-regulates the angiogenetic maturation factor while at the same time down-regulating the angiogenic proliferation factor.

In an aspect of this invention, the first promoter sequence is regulated by a first effector and the second promoter sequence is regulated by a second effector.

In an aspect of this invention, the first and the second effectors are the same.

In an aspect of this invention, the first nucleic acid constructs further comprise a third polynucleotide sequence that encodes a first marker polypeptide or the second nucleic acid construct further comprises a fourth polynucleotide sequence that encodes a second marker polypeptide or the first nucleic acid constructs further comprise a third polynucleotide sequence that encodes a first marker polypeptide and the second nucleic acid construct further comprises a fourth polynucleotide sequence that encodes a second marker polypeptide.

In an aspect of this invention, the first and second marker polypeptides are independently selected from the group consisting of a selection polypeptide and a reporter polypeptide.

In an aspect of this invention, the third and/or the fourth polynucleotide sequences are transcriptionally linked to the first and/or the second polynucleotide sequence.

An aspect of this invention is a method for producing angiogenesis in a tissue of a patient in need thereof comprising administering to the tissue a plurality of a first cell type that has been genetically altered with a first nucleic acid construct comprising a first polynucleotide sequence that expresses or over-expresses a first angiogenic factor; and, administering to the tissue a plurality of a second cell type, which is different from the first cell type, that has been genetically altered with a second nucleic acid construct comprising a second polynucleotide sequence that expresses or over-expresses a second angiogenic factor, wherein the factor expressed or over-expressed by the first cell type enhances the physiology and proliferation of the second cell type and the factor expressed or over-expressed by the second cell type enhances the physiology and proliferation of the first cell type. This aspect of the invention herein may include any of the above aspects as well as those below.

An aspect of this invention is the above method in which the first cell type is endothelial cells and the second cell type is smooth muscle cells wherein the endothelial cells express or over-express an angiogenic maturation factor and the smooth muscle cells express or over-express an angiogenic proliferation factor.

An aspect of this invention is the above method in which the angiogenic maturation factor is Ang-1 and the angiogenic proliferation factor is VEGF.

DETAILED DESCRIPTION OF THE INVENTION

Brief Description of the Tables

Table 1 shows the hemodynamic and histological data obtained 2 weeks following injection of retrovirally-transduced EC and SMC into minipig hind limbs.

Discussion

The present invention relates to the use of autologous or exogenous EC and smooth muscle cells (SMC) that are genetically altered prior to administration to express or over-express pro-angiogenic factors such as, without limitation, VEGF and Ang-1. The cells are implanted at a treatment site in a patient where they secrete the stimulatory factors and induce angiogenesis.

The terms "express" and "over-express" are used to denote the fact that, in some cases, a cell useful in the method herein may inherently express some of the factor that it is to be genetically altered to produce, in which case the addition of the polynucleotide sequence results in over-expression of the factor. That is, more factor is expressed by the altered cell than would be, under the same conditions, by a wild type cell. Similarly, if the cell does not inherently express the factor that it is genetically altered to produce, the term used would be to merely "express" the factor since the wild type cell did not express the factor at all.

By "genetically altered" is meant that the genomic content of the cell is altered to include an exogenous nucleic acid sequence not found in the wild type cell, or an additional copy of an endogenous nucleic acid sequence found in the wild type cell, that encodes a vascular proliferation factor or a vascular maturation factor. The alteration can be stable, as in the case, without limitation, of retrovirus infection where the new sequence in integrated into the genome and is passed from generation to generation or it can be transient as in the case, without limitation, of adenovirus infection wherein the new sequence is not passed on.

Thus, in one aspect, the present invention relates to a nucleic acid expression construct comprising a first polynucleotide segment encoding an angiogenic proliferating factor that promotes EC proliferation and migration and a second polynucleotide segment encoding an angiogenic maturation factor that promotes blood vessel maturation and stabilization. Examples, without limitation, of EC proliferation/migration factors are VEGF (GenBank Accession number AB021221), HGF (GenBank Accession number D14012), PIGF (GenBank Accession number X54936), VEGF-C (GenBank Accession number NM005429), bFGF (GenBank Accession number J04513), aFGF (GenBank Accession number S67291) and Leptin (GenBank Accession number XM045426). Examples, without limitation, of maturation/stabilization factors are Angiopoietin 1 (Ang-1), the TGF-β family (TGF-β1, TGF-β receptor-2, endoglin, Smad5), VE-Cadherin, ephrinB2, PDGF, Bmx tyrosine kinase and MCP-1.

The angiogenic proliferating factor and the angiogenic maturation factor may be expressed from a single promoter sequence in the nucleic acid construct. Various constructs can be used to accomplish this. For example, without limitation, the first and second polynucleotide segments can be transcriptionally fused through a linker sequence that includes an internal ribosome entry site (IRES) sequence. This enables the translation of the polynucleotide segment downstream of the IRES sequence. In this way, a transcribed polycistronic RNA molecule containing the coding sequences of both the angiogenic proliferating factor and the angiogenic maturation factor can be translated from both the capped 5' end and the internal IRES sequence to express the factors.

Alternatively, the first and second polynucleotide segments can be translationally fused through a protease recognition site cleavable by a protease expressed by the cell to be genetically altered. In this case, a single chimeric polypeptide will be expressed and subsequently cleaved by the cell-expressed protease to generate the factors.

It is also an aspect of this invention that the nucleic acid construct comprise two promoter sequences, which may be the same or different. The promoters are isolated from one another so that the angiogenic proliferating factor and the angiogenic maturation factor are separately transcribed, each from its own dedicated promoter.

Of course, expression of the angiogenic proliferating factor and the angiogenic maturation factor can also be directed by two completely separate nucleic acid constructs inserted into the same cell. The promoters used in the two constructs may be the same or different.

The promoters used in these constructs are preferably constitutive, tissue specific or inducible promoters. Constitutive promoters are those that normally operate in a cell at all times; that is they are not, or at least do not appear to be, subject to quantitative regulation. Inducible promoters, on the other hand, are regulatable and their quantitative operation may be controlled by a specific stimulus. The phrase "tissue specific promoter" is self-explanatory; such promoters only operate is specific tissues.

To generate the nucleic acid constructs, the polynucleotide segment encoding the angiogenic proliferating growth factor or the angiogenic maturation factor are ligated into commercially available expression vector systems. Such vector systems can easily be modified using recombinant techniques well-known in the art to replace, duplicate or mutate existing promoter or enhancer sequences and/or to introduce additional polynucleotide sequences such as, without limitation, selection markers or reporter polypeptides.

Suitable mammalian expression vectors include, but are not limited to, pcDNA3, pcDNA3.1(+/−), pZeoSV2(+/−), pSecTag2, pDisplay, pEF/myc/cyto, pCMV/myc/cyto and pCR3.1, all of which are available from Invitrogen. They also include pCI, which is available from Promega, pBK-RSV and PBK-CMV both of which are available from Stratagene, and pTRES which is available from Clontech.

The vector system is used to infect autologous or exogenous vascular cells with the nucleic acid constructs that, in turn, express the angiogenic proliferating and maturation factors.

The nucleic acid constructs are used to genetically alter mammalian cells including, but not limited to, endothelial cells, smooth muscle cells, pericytes, myocytes, monocytes, fibroblasts, peripheral blood progenitors, embryonic stem cells or bone marrow stem cells.

The genetically altered cells are inserted at or near an ischemic tissue to induce angiogenesis therein. Cell insertion can be accomplished in numerous ways, which will become apparent to those skilled in the art based on the disclosures herein. For example, without limitation, a delivery catheter similar to the perfusion catheters manufactured by Boston Scientific (USA) could be used.

The vascular cells themselves, genetically altered as they are to over-express at least one angiogenic proliferating factor and at least one angiogenic maturation factor, are an aspect of this invention. Preferably, the cells are genetically altered ex vivo, although in-vivo genetic alteration of xenogenic tissue followed by cell harvesting can also be used.

As used herein the phrase "genetically altered" refers to a cell transiently or stably transformed with exogenous polynucleotide sequence(s). In stable transformation, the exogenous polynucleotide sequences integrate into the genome of the cell and are genetically inherited by daughter cells. In transient form, the exogenous polynucleotide sequences exist as separate nuclear or cytoplasmic entities and are not genetically inherited by daughter cells.

In an aspect of this invention, at least two types of cells are used in order to mimic as closely as possible normal blood vessel generation and maturation. As noted above, normal angiogenesis is a stepwise process that involves several cell types expressing several angiogenic factors. Cell types which are involved in angiogenesis and therefore may be used in the methods of this invention include, but are not limited to, EC, SMC, pericytes, myocytes and peripheral blood progenitors, bone marrow stem cells and embryonic stem cells. A combination of EC and SMC is presently preferred.

The cells may be genetically altered such that an angiogenic proliferating factor and an angiogenic maturation factor are over-expressed from both cell types. Or one cell type may be genetically altered to over-express both factors while the other cell type is genetically altered to over-express one of the factor. Or one cell type may be genetically altered to express or over-express the proliferating factor and the other cell type may be genetically altered to express or over-express the maturation factor. It is presently preferred that EC and SMC are used, with the EC over-expressing a cell maturation factor and the SMC over-expressing an angiogenic proliferation factor.

The genetically altered cells are administered to a tissue region of an individual to, for example and without limitation, bypass or penetrate an occlusion in a vessel supplying blood to that tissue region. Administration can be directly into the occluded blood vessel or it can be into the tissue surrounding the vessel to generate vascular cell enrichment of the tissue and thereby promote more rapid angiogenesis.

The cells in the methods of this invention may be xenogenic or homogenic. If xenogenic cells are used, measures must be taken prior to or during administration to reduce the possibility of rejection. Numerous methods for accomplishing this are known to those skilled in the art and as such no further detail is provided herein.

The cells are preferably obtained from venous, arterial, peripheral blood or bone marrow tissue of the patient or of a syngenic individual.

As noted previously, angiogenesis is an essentially stepwise process. Thus, certain factors are required at certain times. To mimic the natural process as closely as possible, it is an aspect of this invention to induce angiogenesis in a target tissue by administering a first cell type genetically altered to express at least one angiogenic proliferating factor to a target tissue followed by administration of a second cell type genetically altered to express at least one angiogenic maturation factor. The first cell type is administered from about 12 hours to about 2 weeks prior to the administration of the second cell type.

It is also an aspect of this invention that the genetically altered cells are administered simultaneously and then either allowed to self-regulate or are regulated by promoters and effectors that respond to conditions occurring during angiogenesis. By simultaneously is meant that the cells are administered together; i.e., they are mixed prior to administration or they may be administered sequentially but within a relatively short period of time of one another compared to the above 12 hours to 2 weeks; e.g. within minutes to an hour or so between administrations.

It is a presently preferred embodiment of this invention that the cells be administered in approximately equal quantities, i.e. in about a 1:1 ratio. In this instance, by "about" is meant ±20%. It is understood, however, that any ratio of cells may be used depending on the tissue being treated, the factor and cells being used, etc. Such determination will be readily reached by those skilled in the art based on the disclosures herein.

Another presently preferred embodiment of this invention is to have a first cell type express or over-express a factor that is used by the second cell type and have the second cell type express or over-express a factor that is used by the first cell type, which results in the mutual enhancement of the viability, physiology and proliferation of both cell types in a cross-regulatory manner.

It is also an aspect of this invention to control the release of the various angiogenic factors by using cells that express the factors from a promoter sequence regulatable by an effector.

As used herein, the term "effector" or the phrase "regulatory factor" refers to a molecule or a physical condition (e.g., light, biomechanical stress, etc.) that up-regulates or down-regulates the expression of a polynucleotide sequence by its action on a regulatable promoter. Regulatable promoters that can be used in the methods of the present invention include chemically regulated promoters such as, without limitation, the tetracycline regulatable promoter described in Agha-Mohammadi S and Lotze MT, "Regulatable systems: applications in gene therapy and replicating viruses," *J Clinical Investigations*, 2000, 105:1177). There, it was demonstrated that VEGF expression is down-regulated by tetracycline whereas Ang-1 expression is up-regulated. Thus, cells (same or different) containing both factors could be administered to a patient. The cells would are allowed to express VEGF for a time to encourage cell proliferation. Then tetracycline is administered to down-regulate VEGF expression and up-regulate Ang-1 expression to promote cell maturation.

Biomechanically regulated promoters such as, without limitation, the shear stress responsive promoter described in *PNAS USA*, 1993, 90:4591-4595 can also be used.

Thus, an aspect of the present invention is one or more vascular cells that are genetically altered with two or more nucleic acid constructs that express at least two or more angiogenic factors from regulatable promoters. The angiogenic factors are selected such that at least one is an cell proliferation/migration factor and at least one is a maturation/stabilization factor. The promoters from which the factors are expressed are selected such that, following administration of the cell to the tissue region to be treated, the expression of the factors can be up-regulated or down-regulated to produce a temporal expression pattern that will optimize formation of new blood vessels. The expression of the angiogenic proliferating factor can be regulated by a first regulatory factor and the expression of the angiogenic maturation factor can be regulated by a second regulatory factor. The regulatory factors themselves can be selected so as to generate a different expression pattern for each of the angiogenic factors. Alternatively, a single regulatory factor can be used that up-regulates expression of the angiogenic maturation factor and simultaneously down-regulates expression of the angiogenic proliferating factor.

The promoters are selected such that they can be regulated in vivo, that is, after the cells containing them have been inserted into the tissue to be treated. Thus, promoters that are regulatable by biological conditions generated during, or by other conditions compatible with, angiogenesis, are presently preferred. Such conditions include, without limitation, forces associated with cell/cell interactions during new blood vessel formation. Promoters regulated by external factors administered either directly to the target tissue or that can be placed in the blood stream to reach the target tissue through the circulatory system can also be used.

Once cells have been transduced, the expression of the factors can be easily checked. For example, VEGF and Ang-1 levels in transduced EC can be measured in supernatant collected from cultures of genetically modified cells over a 24-hour period using ELISA and western blot analysis.

The present invention avoids gene transfer in a patient's body or the release of viral vectors into the blood stream. Enrichment of ischemic tissue is accomplished using vascular cells genetically altered to over-express factors that improve cell survival while promoting blood vessel formation. The coordinated use of EC and SMC and the expression of two different genes, one from each cell type, ensures cooperation between administered and recruited cells in the formation and maintenance of blood vessels.

Thus, the present invention provides methods that can be used to promote the generation of new blood vessels or the re-canalization of occluded or narrowed vascular tissue regions. It is substantially less invasive than bypass surgery or angioplasty and avoids the risks associated with such procedures.

An added advantage of the present invention is that the coordinated expression of one gene by genetically altered EC and a different gene by genetically altered SMC ensures cooperation between administered and recruited cells in the formation and maintenance of new blood vessels. Finally, it should be noted that the approach of the present invention, i.e., the administration of fully competent cells provides the added benefit of resulting in cellular enrichment of the vascular bed where endogenous cells may be weakened by ischemia caused by the vascular disease or damage.

EXAMPLES

The nomenclature and laboratory techniques used herein are well-known to those skilled in the molecular biological, biochemical, microbiological and recombinant DNA arts. For example, see "Molecular Cloning: A laboratory Manual," Sambrook et al., (1989); "Current Protocols in Molecular Biology," Volumes I-III, Ausubel, R. M., ed. (1994); Ausubel, et al., "Current Protocols in Molecular Biology," John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980). Useful immunoassays are described in the patent literature (for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521). Likewise, the literature n the field provides substantial experimental direction, e.g., "Oligonucleotide Synthesis"Gait, M. J., ed. (1984); "Nucleic Acid Hybridization," Hames, B. D., and Higgins S. J., eds. (1985); "Transcription and Translation," Hames, B. D., and Higgins S. J., eds. (1984); "Animal Cell Culture," Freshney, R. I., ed., (1986); "Immobilized Cells and Enzymes," IRL Press, (1986); "A Practical Guide to Molecular Cloning," Perbal, B., (1984); "Methods in Enzymology," Vol. 1-317, Academic Press; "PCR Protocols: A Guide To Methods And Applications", Academic Press, San Diego, Calif. (1990); Marshak, et al., "Strategies for Protein Purification and Characterization—A Laboratory Course Manual," CSHL Press (1996). The patents and pending applications cited above are incorporated by reference as if fully set forth, including any drawings, herein.

Example 1

Preparation of Ang-1 cDNA

The Ang-1 cDNA was reverse transcribed using AMV reverse transcriptase (RT) (Promega) from total RNA extracted from human saphenous vein SMC. The resulting cDNA was amplified using the expand high fidelity PCR system kit (Roche). The primers used were 5'-AGATCT-TCAAAAATCTAAAGGTCGAAT-3' and 5'-AGATCT-GCTGGCAGTACAATGACAGTT-3' (the underlined sequences represent the BglII restriction sites used for cloning). The 1500 bp Ang-1 cDNA was sub-cloned into pGEMT-easy vector (Promega) by TA cloning. Both strands of the PCR product were sequenced and found 100% identical to the published sequence.

Example 2

Preparation of Bicistronic Pseudo Typed Retroviral Vectors

The following packaging cells lines were used as required to prepare the complete virions using techniques well-known to those skilled in the art and, therefore, not requiring further description herein.

The 293-FLY Packaging Cell Line is a human embryonic kidney (HEK 293)-derived packaging cell line designed for rapid, transient and stable production of high-titer retrovirus. Blasticidin and Phleomycin resistance genes were used to separately introduce the viral gag-pol and env genes (Cosset F L et al. J Virol 1995). 293-FLY-A cells express an amphotropic envelope, and thus viral vectors produced by these cells can infect a broad range of mammalian cell types via RAM1 (Pit2) receptor (Miller A D. & Chen F. J. Virol, 1996). 293-FLY-GALV cells express gag-pol from Mo-MuLV and gibbon ape leukemia virus (GALV) envelope glycoproteins. Viral vectors produced by these cells can enter target cells via GALV (Pit1) receptor (Marandin A et al. Human Gene Ther 1998). 293-FLY-10A cells express a dualtropic (or polytropic) envelope that recognizes receptors on mouse, rat, human, hamster, mink, cat, dog, and monkey cells. Viral vectors produced by these cells can enter target cells via two surface molecules, the amphotropic retrovirus receptor, RAM1 (Pit2), and the GALV (Pit1) receptor (Miller, A. D. & Chen, F. J. Virol, 1996).

The 293 pCL-Eco packaging cell line is a human embryonic kidney (HEK 293)-derived cell line that express an ecotropic envelope, and thus virus produced by these cells can infect the mouse PA317 cell Line (Naviaux, J Virol 1996, Miller, Methods Enzymol 1993).

The PA317 packaging cell line packaging cell line is an amphotropic retrovirus packaging cell line in which the gag, pol, and env genes of the helper virus are separated on two different plasmids. A plasmid containing the MMLV gag and pol gene was transfected into NIH 3T3 cells, and a plasmid containing the 4070A amphotropic env gene was transfected into the resulting clone, and thus virus produced by these cells can infect a broad range of mammalian cell types via RAM1 (Pit2) receptor (Markowitz D, et al. Virology. 1988).

The TE-FLY-GALV cell line is a human rhabdomyosarcoma derived cell line designed for rapid, transient and stable production of high-titer retrovirus (S. Chapel-Fernandes and F. L. Cosset, unpublished data, 1998). TE-FLY-GALV cells express gag-pol from Mo-MuLV and GALV env.

The 293FLY-A, 293FLY-GALV, 293-FLY-10A, and TEFLY-GALV packaging cell lines were maintained in D10 medium (high-glucose Dulbecco's modified Eagle's medium supplemented with 10% fetal calf serum, Glutamine 2 mM, penicillin 100 units/ml, and streptomycin0.1 mg/ml) supplemented with the antibiotics Blasticidin 6 µg/mi and Phleomycin 10 µg/ml. The 293 pCL-Eco and PA317 lines were maintained in D10 medium alone.

Recombinant retroviral vectors expressing the human $VEGF_{165}$, and/or the EGFP genes were constructed by cloning the expression cassette into pLXSN plasmid (# K1060-B Clontech, USA). Construction of pLXSN-VEGF-EGFP, a bicistronic plasmid co-expressing both genes, was done in two steps. First a 600 bp BamH1 fragment of $VEGF_{165}$ was inserted into BamH1 site in pIRES2-EGFP (#6029-1 Clontech, USA). Second, a 2.0 kB EcoRI-Munl fragment containing $VEGF_{65}$, IRES element and the EGFP genes was excised from pVEGF-IRES-EGFP plasmid and inserted into the EcoRI restriction site inside the multiple cloning site of pLXSN. For construction of the control plasmid pLXSN-IRES-EGFP, an IRES-EGFP EcoRI-Hpal fragment (1400 bp) was excised from pIRES2-EGFP and inserted into EcoRI-Hpal sites in PLXSN. The bicistronic recombinant retroviral vector pLXSN-Ang-1-IRES-EGFP was constructed by cloning the Ang-1 EcoRI fragment into EcoRI cut PLXSN-IRES-EGFP plasmid. All expression cassettes were regulated by the Mo-MULV 5' long terminal repeat (LTR).

For the retroviral $VEGF_{165}$, and/or the EGFP vectors production, 5 µg of PLXSN-EGFP or pLXSN-VEGF-EGFP plasmids DNA were transiently transfected into 293E3 ecotropic packaging cells. After 48 hours the supernatant from confluent cultures were collected, filtered (0.45 µm) and added to PA317 amphotropic packaging cells. Transduced PA317 cells were grown under G418 selection (300 µg/ml) and supernatant from the stable cells was collected and used to transduce TEFLYGA packaging cells which express GALV envelope glycoprotein to generate pseudo typed virus (Cosset F L, J. Virol. 1995). After G418 selection (400 µg/ml) of transduced TEFLYGA cells, individual colonies were collected and screened for EGFP expression using fluorescent microscopy.

For the retroviral Ang-1 and EGFP vector production, 5 µg of pLXSN-Ang-1-EGFP plasmids DNA were transiently transfected into 293-FLY-A packaging cells. After 48 hours the supernatant from confluent cultures were collected, filtered (0.45 µm) and added to 293-FLY-GALV packaging cells. Transduced 293-FLY-GALV cells were grown under G418 selection (300 µg/ml). Stable individual colonies were collected and screened for EGFP expression using fluorescent microscopy. VEGF and Ang-1 expression was confirmed by RT-PCR and western analysis. Viral titers of each colony were determined by transduction of TE671 cells. Colonies producing $10^6$ ffu/ml were used in our experiments.

Example 3

Vascular Cells Isolation, Expansion and Transduction

Autologous EC and SMC were isolated from a 5-10 cm segment of human saphenous or miniature pig jugular vein. EC harvesting was performed using incubation with collagenase 1 mg/ml for 15 min at 37° C. (Weisz A, Circulation, 2001). EC were identified based on their morphology of monolayer and cobblestone appearance under light inverted microscopy. Assurance of EC identification was done using immunohistochemical staining for the EC specific marker, vWF. Isolated EC were cultured in M199 supplemented with 20% fetal calf serum, penicillin 100 units/ml, streptomycin 0.1 mg/ml, amphotericin B 2.5 µg/ml, L-glutamate 2 mM, bFGF 2.5 ng/ml, and heparin 100 units/ml.

SMC were isolated by explant outgrowth from 2×2 mm pieces of vein segment incubated on fibronectin coated plates. SMC were identified based on their morphology of spindle shape and "hills & valley" appearance under light inverted microscopy. Assurance of SMC identification was done using immunohistochemical staining for the SMC specific marker αSMC actin. Cells were cultured in Dulbecco's Modified Eagles Medium (DMEM) supplemented with 10% fetal calf serum, L-glutamine 2 mM, penicillin 100 units/ml, streptomycin 0.1 mg/ml, amphotericin B 2.5 µg/ml, bFGF 2 ng/ml and heparin 100 units/ml.

Transduction of vascular cells was performed using retroviral vectors according to standard methods (Kahn M, Circ Res 1992). EC or SMC ($5 \times 10^5$ cells) at passage 3-6 after harvesting were seeded on 60 mm fibronectin-coated plates 24 hr prior to viral transduction. One hour prior to transduction, the medium was replaced with serum-free M199 medium containing 0.1 mg/ml of the cationic polymer DEAE-dextran (Sigma, USA). Following pre-conditioning, the cells were washed three times with phosphate-buffered saline (PBS). Transduction was performed by incubation of the cells for 4 hours, with supernatants containing viruses collected and filtered (0.45 µm) freshly from the virus producing packaging cell lines. At the end of the incubation period the vector-containing medium was replaced with EC or SMC growth medium, respectively. Genetically modified cells were grown in G418 selection medium for 2-4 days until at least 90% of the expressed the transduced genes. Transduced cells were monitored for GFP and trans-gene expression.

Ang-1 or $VEGF_{165}$ protein expression by retroviral transduced vascular cells is detected using Western blot analysis of the conditioned medium. 48 hours post infection the medium was changed to serum free medium and cells were grown for additional 48 hours. Samples of the conditioned medium (30 µl) were separated on 10% (for Ang-1), 12% (for VEGF) or 8% (for SDS polyacrylamide gel under reducing conditions, and electrotransferred to nitrocellulose membrane. The blots were blocked with 0.1% skim milk in TBS containing 0.3% tween-20 (TBST) for 1 hour at room temperature using gentle agitation. The blots were incubated with primary antibody diluted in blocking solution for 2 hours at room temperature. 1:500 dilution of polyclonal goat anti-Ang-1 antibody (#SC-6319 Santa Cruz) was used for Ang-1 detection and polyclonal rabbit anti-VEGF165 antibody (#SC 152 Santa-Cruz, USA) (1:700) was used for VEGF detection. Following the incubation the blots were washed three times with TBST and incubated for 1 hour at room temperature with anti rabbit peroxidase-conjugate antibody (Sigma) diluted 1:7000 in TBST for VEGF or anti goat peroxidase-conjugate antibody (Sigma) diluted 1:10000 in TBST for Ang-1. After three washes with TBST bound antibody was visualized using the ECL reagents (Sigma) and exposed to X-ray film.

Example 4

In Vitro Angiogenesis

In-vitro angiogenesis was examined using endothelial cell (EC), smooth muscle cell (SMC), and mixed EC and SMC co-culture sprouting from spheroids in collagen three-dimension matrix. A mixture of retroviral vector-transduced EC and SMC (375 cells of each cell type) containing spheroids were constructed and the sprouting of endothelial as well as SMC from spheroids of cells implanted in collagen was estimated. Pseudo-typed retroviral vectors encoding $VEGF_{165}$-IRES-GFP, Ang-1-IRES-GFP, or GFP alone as control were used to transduce primary human saphenous EC or SMC. EC were tagged with Dil-291 red fluorescent marker prior to mixing, to differentiate between SMC and EC in the mixed spheroids. In brief, the retrovirally-transduced EC and/or SMC were suspended in culture medium containing 0.25% (w/v) carboxymethylcellulose and seeded in non-adherent round-bottom 96-well plates (Nunc). During a 24 h incubation (37° C., 5% $CO_2$), the suspended cells form a single spheroid per well of defined size and cell number. The spheroids generated were then embedded in collagen gels. A collagen stock solution was prepared prior to use by mixing 8 vol acidic collagen extract of rat tails (equilibrated to 2 mg/ml, 4° C.) with 1 vol 10XM199 (Gibco BRL), 1 vol neutralization solution containing 0.34 N NaOH and 7.5% $NaHCO_3$ to adjust the pH to 7.4. This stock solution (0.5 ml) was mixed with 0.5 ml room temperature medium M199 with 40% human serum containing 0.5% (w/v) carboxymethylcellulose to prevent sedimentation of spheroids before polymerization of the collagen gel. The spheroid (20-30) containing gel was rapidly transferred into pre-warmed 24-well plates and allowed to polymerize. The gels were incubated at 37° C., 5% $CO_2$ and documented by digital video camera (DXM1200 Nikon, Japan).

Some sprouting was observed when both cell types were transduced with control vector (GFP encoding vectors). In the combination of VEGF transduced SMC and control vector-transduced EC, strong enhancement of SMC sprouting non-coordinated with improved EC sprouting was observed. When EC were transduced with Ang-1 and SMC were transduced with control vector, mostly some enhanced sprouting of the endothelial cells was observed. Spheroids containing VEGF-expressing SMC and Ang-1-expressing EC in a 1:1 ratio induced the strongest sprouting response in the EC. Sprouts containing EC also contained attached SMC (coordinated sprouting). When the reciprocal approach was taken, i.e., spheroids containing a mixture of VEGF-expressing EC and Ang-1-expressing SMC, very little sprouting of EC was observed, and autonomous sprouting of SMC occurred. Thus, the use of EC expressing or over-expressing Ang-1 and SMC expressing or over-expressing VEGF is presently preferred.

Example 5

In Vivo Angiogenesis Model

Six miniature pigs were used for the in vivo study. The goal was to test whether injection of genetically modified EC and SMC increases blood flow in an ischemic hind limb model, and whether the increase in blood flow is associated with arteriogenesis. A single dosing regimen was employed. In order to render the experimental protocol clinically relevant the time of autologous cell expansion was limited to 14 days. Autologous cell numbers could be expanded to $5 \times 10^6$ cells (endothelial and smooth muscle cells) in this time period.

Endothelial and smooth muscle cells were isolated and their identity confirmed as outlined above. After confirmation of both cell types, the cells were expanded and transduced with pseudo-typed retroviral vectors. SMC were transduced with $VEGF_{165}$-GFP encoding vector and EC were transduced with Ang-1-GFP encoding vector. Ang-1 or $VEGF_{165}$ protein expression by the retrovirally transduced cells was confirmed by Western blot analysis of the conditioned medium. Then, $5 \times 10^6$ transduced EC and $5 \times 10^6$ transduced SMC were trypsinized, washed to remove serum and any growth-medium supplements, and mixed in 3 ml of saline. The side branches were identified and then the cells were injected into one of them. The other limb, serving as control, was injected with 3 ml of saline. Selective angiography was performed on both sides to determine whether capillary occlusion occurred after cell injection. Blood flow was measured at the stump of the femoral artery on both sides using a Doppler flow meter.

Evaluation of tissue perfusion in the ischemic hind limb was performed two weeks after cell injection. Blood flow was again measured at the stump of the femoral artery using a Doppler flow meter. Differences in flow were regarded as an indication of angiogenesis. Selective angiography was performed on both sides to assess collateral vessel formation. Ten muscle biopsies were taken from both limbs, from a region adjacent to the site of connection of the side branch and the distal femoral artery. The muscle biopsies were processed to identify number of arterial blood vessels. Muscle biopsies from the region supplied by the side branch were stained using actin and Movat staining to identify arterial vessels with (muscular arteries) and without (arterioles) elastic membranes.

The hemodynamic and histology data from the two hind limbs of the 6 miniature pigs are summarized in Table 1. The findings in the following table represent flow increased as a result of cell injection.

The number of arterioles, counted in all muscle biopsies and standardized to muscle area, was significantly increased. The number of muscular arteries as counted in all muscle biopsies and standardized to muscle area tended to increase but the difference did not reach statistical significance. The total number of arterial vessels as counted in all muscle biopsies and standardized to muscle area increased significantly.

All animals survived the procedures. No clinical adverse events, such as acute limb ischemia, weight loss or wound infection was observed. The hematological profile as well as liver and kidney functions were all normal.

TABLE 1

|  | Cell Injection | No Cell Injection | p value |
|---|---|---|---|
| Femoral stump blood flow ml/min | 96 ± 34 | 45 ± 33 |  |
| Number of arterioles/mm² muscle | 0.29 ± 0.08 | 0.20 ± 0.03 | 0.04 |
| Number of muscular arteries/mm² muscle | 0.06 ± 0.01 | 0.05 ± 0.02 | 0.38 |
| Total number of arterial vessels/mm² muscle | 0.35 ± 0.08 | 0.25 ± 0.03 | 0.026 |

CONCLUSION

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All patents, patent applications and sequences disclosed therein and/or identified by a GenBank accession number mentioned in this specification are herein incorporated in their entirety by reference into the specification, to the same extent as if each individual publication, patent, patent application or sequence was specifically and individually indicated to be incorporated reference. In addition, citation or identification of any reference in this on shall not be construed as an admission that such reference is available as to the present invention.

Other embodiments may be found in the claims that follow.

What is claimed is:

1. A method for inducing the formation and maturation of new blood vessels in a tissue of a patient that requires angiogenesis, the method comprising:
simultaneously injecting directly into an artery of said tissue, cells in about a 1:1 ratio
i) autologous smooth muscle cells comprising a nucleic acid construct comprising a polynucleotide sequence encoding vascular endothelial growth factor (VEGF) operably linked to a promoter such that said smooth muscle cells over-express VEGF; and,
ii) autologous endothelial cells comprising a nucleic acid construct comprising a polynucleotide sequence encoding angiopoietin-1(Ang-1) operably linked to a promoter such that said endothelial cells over-express Ang-1,
thereby inducing the formation and maturation of new blood vessels in the tissue of said patient.

2. The method of claim 1, wherein the tissue is isehemic tissue, a narrowed or occluded vascular conduit or an injured vascular tissue.

3. The method of claim 2, wherein the narrowed or occluded vascular conduit is a narrowed or occluded artery, narrowed or occluded vein, or a narrowed or occluded synthetic graft.

* * * * *